(12) United States Patent
Rothstein et al.

(10) Patent No.: US 8,801,706 B2
(45) Date of Patent: Aug. 12, 2014

(54) PARAVALVULAR LEAK CLOSURE DEVICES AND METHODS

(75) Inventors: Paul T. Rothstein, Elk River, MN (US); Cathleen A. Bergin, Hugo, MN (US); Cynthia T. Clague, Minnetonka, MN (US); Michael M. Green, Forest Lake, MN (US); Alexander J. Hill, Blaine, MN (US); James R. Keogh, Maplewood, MN (US); Timothy G. Laske, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1139 days.

(21) Appl. No.: 12/771,031

(22) Filed: Apr. 30, 2010

(65) Prior Publication Data

US 2011/0054466 A1 Mar. 3, 2011

Related U.S. Application Data

(60) Provisional application No. 61/237,363, filed on Aug. 27, 2009.

(51) Int. Cl.
*A61B 18/18* (2006.01)

(52) U.S. Cl.
USPC .............................................. 606/41; 606/45

(58) Field of Classification Search
USPC ....................................................... 606/32–45
See application file for complete search history.

(56) References Cited

U.S. PATENT DOCUMENTS

| | | |
|---|---|---|
| 2005/0101950 A1 | 5/2005 | Gough et al. |
| 2005/0245926 A1 | 11/2005 | Edwards et al. |
| 2008/0287944 A1 | 11/2008 | Pearson et al. |

*Primary Examiner* — Linda Dvorak
*Assistant Examiner* — Amanda Scott

(57) ABSTRACT

An ablation catheter including an inner tube having a length, a distal end and a longitudinal axis, a plurality of needles extending from the distal end of the inner tube and biased away from the longitudinal axis, an outer sheath slideably moveable relative to the inner tube to surround at least a portion of the length of the inner tube and its extending needles, and a radio frequency energy source electrically connected to the plurality of needles.

9 Claims, 9 Drawing Sheets

PARAVALVULAR LEAK CLOSURE DEVICES AND METHODS

CROSS-REFERENCE TO RELATED APPLICATION

This application claims the benefit under 35 U.S.C. §119(e) of U.S. Provisional Patent Application No. 61/237,363, filed Aug. 27, 2009, which is incorporated herein by reference in its entirety.

TECHNICAL FIELD

The present invention relates to devices and methods for repairing paravalvular leaks. In particular, the present invention relates to devices and methods for repairing paravalvular leakage using radio frequency (RF) energy.

BACKGROUND

Diseased or otherwise deficient heart valves can be repaired or replaced using a variety of different types of heart valve surgeries. One general type of heart valve surgery involves an open-heart surgical procedure that is conducted under general anesthesia, during which the heart is stopped and a heart-lung bypass machine controls blood flow. This type of valve surgery is highly invasive and exposes the patient to a number of potential risks, such as infection, stroke, renal failure, and adverse effects associated with use of the heart-lung machine, for example. Due to the drawbacks of open-heart surgical procedures, there has been an increased interest in minimally invasive and percutaneous replacement of cardiac valves. Such surgical techniques involve making a relatively small opening in the skin of the patient into which a valve assembly is inserted and delivered to the heart via a delivery device similar to a catheter. This technique is often preferable to more invasive forms of surgery, such as the open-heart surgical procedure described above.

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, prosthetic heart valve designs attempt to replicate the function of the valve being replaced and thus will include valve leaflet-like structures used with either bioprostheses or mechanical heart valve prostheses. If bioprostheses are selected, the replacement valves may include a valved vascular segment that is mounted in some manner within an expandable stent frame to make a valved stent. In order to prepare such a valve for percutaneous implantation, one type of valved stem can be initially provided in an expanded or uncrimped condition, then crimped or compressed around a balloon portion of a catheter until it is as close to the diameter of the catheter as possible. In other percutaneous implantation systems, the stem of the valved stent can be made of a self-expanding-material. In either case, the shape of the stent frame in its expanded condition will typically be at least slightly different than the shape of the implantation site, therefore creating the potential for gaps or spaces between the stent frame and the implantation site that allow for paravalvular leakage. For one example, placing a circular aortic stem in an aortic annulus that has a non-circular shape may result in a gap between the stem and the aortic wall, thereby creating the potential for paravalvular leakage.

With an increasing number of valve replacements being performed using a percutaneous or transcatheter valve delivery approach, it is desirable to provide methods and devices for repairing paravalvular leakage, particularly those that can allow for repairing the leaks in a percutaneous manner. However, it is also desirable to provide methods and devices for repairing paravalvular leakage for valves that have been surgically implanted.

SUMMARY

In one aspect of the invention, transcatheter methods and devices are provided for closing or repairing a leak around a stented valve using RF energy. These devices and methods can be used in cases where the valve was delivered in a transcatheter manner, or can also be used to close a leak around a valve that has been implanted surgically.

In one aspect of the invention, an ablation catheter is provided with an inner tube having a central lumen for guidewire insertion, and at least one needle electrode extending from a distal end of the inner tube. The catheter is further provided with an outer tube or sheath that is moveable relative to the inner tube so that the needles of the inner tube can be at least partially covered or surrounded by the outer tube. The catheter is insertable into the patient using visualization techniques until the catheter reaches the area of the paravalvular leakage. The various components of the system can be manipulated relative to each other until the needles are in a desired position within the leak opening. The needles can then be moved to penetrate the stent and adjacent surrounding tissue, and then the needles can be moved relative to each other to pull the tissue and stent into closer proximity to each other. Radio frequency energy can then be applied to the one or more needle electrodes to weld tissue together and/or shrink tissue, thereby closing, modifying, or minimizing the size and/or shape of the leak opening. This procedure can be repeated multiple times with the same or different ablation catheters to provide the desired sealing of the leak area, particularly in applications where the leak area is relatively large.

In one aspect of the invention, an ablation catheter is provided, comprising an inner tube having a length, a distal end, and a longitudinal axis; a plurality of needles extending from the distal end of the inner tube and biased away from the longitudinal axis; an outer sheath slideably moveable relative to the inner tube to surround at least a portion of the length of the inner tube and its extending needles; and a radio frequency energy source electrically connected to the plurality of needles.

In another aspect of the invention, a method of reducing the size of a space between an implanted device and an adjacent tissue within a patient is provided. The method comprises the steps of: inserting an outer sheath into the patient until a distal end of the outer sheath is positioned adjacent to the space; inserting an inner tube into a proximal end of the outer sheath, wherein the inner tube comprises a plurality of needles extending from its distal end; guiding the inner tube through the outer sheath until the needles extend at least partially from the distal end of the outer sheath; positioning the tips of the needles adjacent to the tissue and the implanted device: advancing the needles until they penetrate the tissue and interface with the implanted device: retracting the needles at least partially relative to the sheath to pull the tissue and implanted device closer to each other and reduce the size of the space; applying radio frequency energy to at least one of needles; retracting the needles from the tissue: and removing the inner tube and outer sheath from the patient. It is contemplated, however, that the needles need not interface with the implanted device, but that they instead interface with only the tissue adjacent to the implanted device to shrink the tissue to decrease the size of the gap between the tissue and the implanted device.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
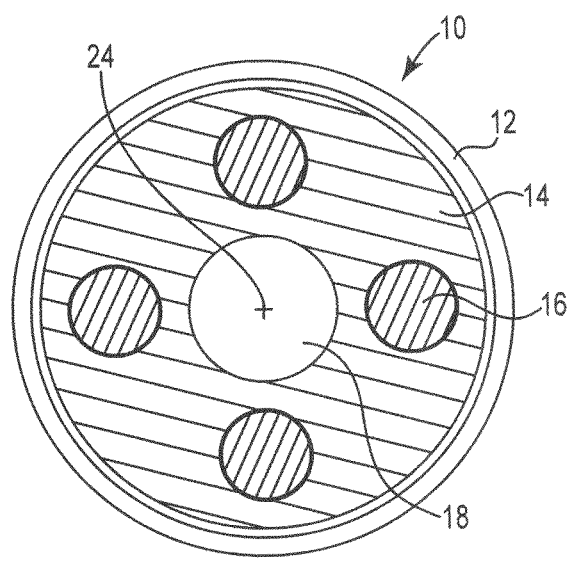
FIG. 1 is a cross-sectional end view of an ablation catheter in accordance with the invention.

Referring now to the Figures, wherein the components are labeled with like numerals throughout the several Figures, and initially to FIG. 1, one embodiment of a section through the working length of an ablation catheter 10 is illustrated. In general, the working length of the ablation catheter 10 includes an outer tube or sheath 12, which can be made of a flexible material such as nylon, PTFE, PEBAX, or the like, or any combination or blend of such materials. Additionally, sheath 12 can be reinforced with a braid, coil, or other structure to increase its radial stiffness. Outer tube or sheath 12 can at least partially surround an inner tube 14 that is preferably made of a flexible, insulating material, although it can be made of a different type of material. The inner tube 14 includes at least one needle opening or depression 16, each of which is sized to mate with a proximal end of an ablation element: such as a needle or needle electrode. Although four of such needle openings are shown in this figure, it is understood that more or less of these openings 16 can be provided, in order to correspond to the number of needles that are provided. The inner tube 14 further may include a central lumen 18, which extends through at least a portion of its length. A guidewire or other component can be moved through this central lumen 18, as will be described in further detail below.

Figure 2:
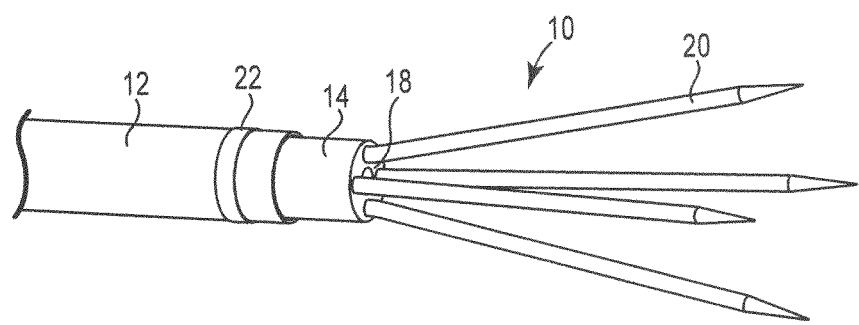
FIG. 2 is a perspective view of a distal end portion of an ablation catheter.

With reference to FIG. 2, a perspective view of the distal end of the ablation catheter 10 is shown. In this Figure, a tip portion of an ablation element or a needle 20 extends from each of the needle openings 16. The needles 20 can be made from a conductive material such as Nitinol, stainless steel, surgical steel, platinum copper, or electrically conductive polymers, for example. One or more portions of needles 20 can be made from a flexible material, a rigid material, and/or a shape memory material, such as Nitinol. The needles 20 can be identical in structure and size to each other for a particular ablation catheter, or at least some of the needles can be differently sized, shaped, and/or configured from each other for a particular ablation catheter in order to provide certain processing capabilities for the system.

The needles 20 can be solid, as shown, or can be tubular or hollow including one or more openings to provide a fluid path that can be used during the ablation process for irrigation fluids, ablation fluids, biological agents and the like. The fluid path in the needles may also be used for transmitting suction to help grasp adjacent tissue. Providing one or more fluid paths in the needles can be desirable for applications where it is desired to irrigate the ablation site with fluid, which may be, for example, any suitable fluid such as saline, an ionic fluid that is conductive, or another conductive fluid. The irrigation fluid can further be used to cool the needle electrode through which it is being delivered. In one embodiment, saline solution can be used as the irrigation fluid. Alternatively, other energy-conducting liquids, such as Ringer's solution, ionic contrast, or blood, may be used. Further, one or more diagnostic agents, therapeutic agents, gene therapy agents, and/or biological agents may be delivered before, with, or after delivery of the irrigating fluid. The irrigating fluid is desirably a sterile fluid.

In situations where an ionic fluid is used as an irrigation fluid, this fluid can electrically couple one or more electrodes of the ablation device 10 to the tissue to be ablated, thereby lowering the impedance at the ablation site. An ionic irrigation fluid may further create a larger effective electrode surface and may be used to cool the surface of the tissue being ablated.

The source for any fluids, such as irrigation fluids, can include a manual or electric pump, an infusion pump, a syringe pump, a syringe, or the like. The fluid or irrigation source may be powered by AC current. DC current, or battery powered, and may include one or more regulators, valves, conduits, tubes, and hoses, for example. In one embodiment, the fluid source may be incorporated into an ablation device 10.

Each of the needles 20 can be secured within one of the openings 16 of the inner tube 14 in any of a number of different ways. For example, one or more adhesives can be used between the outer surface of a needle 20 and the inside surface of an opening 16 to secure the outer surface of each needle 20 to the inner surface of its respective needle opening 16. In an alternative embodiment, the overall length of each needle is long enough that a substantial anchoring portion can be positioned within the inner tube 14 while the desired needle length extends from the end of the inner tube 14. In such an embodiment, adhesives or other materials may not be necessary to secure the needles 20 to the inner tube 14. Rather, the portion of each needle 20 that is inside an opening 16 can be secured in some other way within the catheter 10 (e.g., a retaining collar) or the length of the needle itself may keep it secure within its opening 16 without any additional attachment devices or materials. It is further contemplated that the inner tube 14 does not have any needle openings or depressions 16 and instead has a relatively flat surface at its distal end to which the needles can be attached, such as with adhesives, welding, or the like. In one embodiment, the needles 20 are secured to the inner tube 14 in such a way that they cannot rotate relative to the inner tube 14. Further, the method of securing the needles 20 to the inner tube 14 can be implemented to prevent the needles from prematurely compressing relative to each other and toward a central axis 24 of the catheter 10.

One or more portions of needles 20 can be biased outwardly (i.e., spring biased) relative to the central longitudinal axis 24 of the catheter 10. For example, the tips of the needles 20 can be biased toward the inner surface of the outer tube 12, such that if the outer tube 12 is slid toward the distal end of the catheter 10, the needles 20 will contact the inner surface of the outer tube 12. The outward bias of the needles 20 should not be so strong, however, that it is difficult to move them toward the central axis 24 of the device with the outer tube 12.

Figure 16:
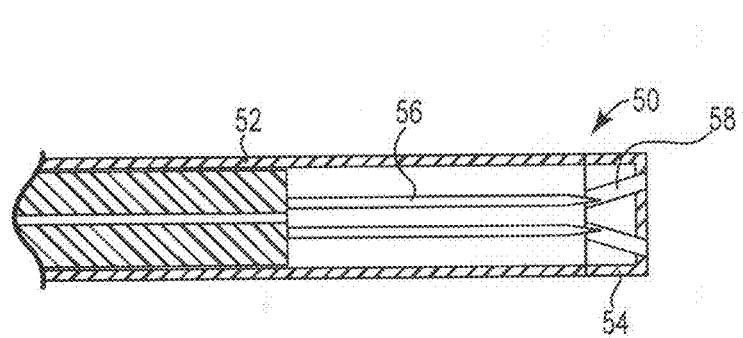
FIG. 16 is a schematic cross-sectional side view of a distal end portion of an ablation catheter of the invention.
Figure 17:
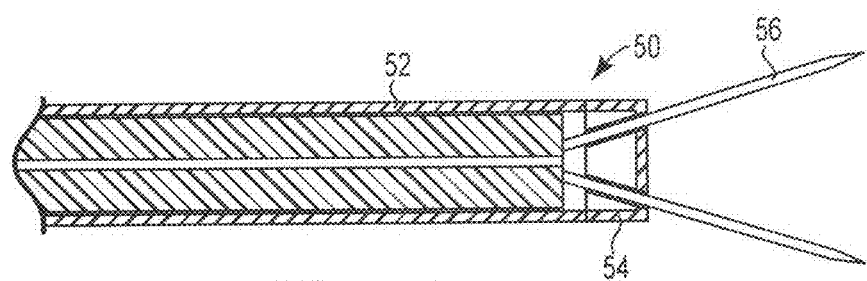
FIG. 17 is a schematic cross-sectional side view of the portion of the ablation catheter of FIG. 16 with its needles in a deployed condition.
Figure 18:
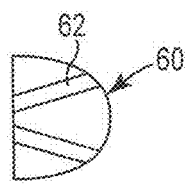
FIG. 18 is a cross-sectional side view nose cone portion for use with an ablation catheter of the invention.

FIGS. 16-18 illustrate additional embodiments of a distal end portion of an ablation catheter that provide alternate manners of biasing or directionally controlling the needles relative to a longitudinal axis of their respective ablation catheters. In particular, FIG. 16 illustrates a distal end of an ablation catheter 50 that comprises an outer tube 52 with a nosepiece 54 coupled to its distal end, and multiple needles 56 attached to an inner tube 55, such as by using the manners of attachment described above, for example. Inner tube 55 may further include a central lumen, which extends through at least a portion of its length. A guidewire or other component can be moved through this central lumen, if desired. Although two needles 56 are illustrated in this embodiment, more or less than two needles 56 can instead be provided. The nosepiece 54 includes multiple channels 58, each of which corresponds to one of the needles 56 and may further include a central lumen (not shown) that is generally aligned with the central lumen of the inner tube 55 and can accommodate a guidewire.

Needles 56 are shown as extending only slightly into the channels 58 in FIG. 16 and in a further deployed position in FIG. 17 where they extend beyond the distal end of the catheter 50 for use in the ablation procedures described herein. The channels 58 of the nosepiece 54 can be provided at the angle at which it is desired for the needles 56 to extend relative to the longitudinal axis of the ablation catheter 50. That is, the channels 58 can all have the same or different angles relative to the longitudinal axis of the catheter in order to directionally control the deployed needles. FIG. 18 illustrates yet another alternative nosepiece 60 that has a curved end shape and multiple channels 62. Although the illustrated nosepieces all include multiple channels, it is understood that a nosepiece may instead only include a single channel. Such an embodiment would include only a single ablation needle.

The ablation catheter 10 may include a needle configuration in which one or more needles 20 include at least two pieces that are hinged or otherwise moveable relative to each other. That is, at least one of the needles can include a first portion that extends in a relatively linear manner from the inner tube 14 to be generally parallel to the central, longitudinal axis of the tube 14, and a second portion of the needle can be moveably attached relative to a distal end of the first needle portion. In such a configuration, the second portion of the needle can be biased generally outwardly relative to the central longitudinal axis of the inner tube when in their released or extended configuration. The outward bias can be provided either by the materials from which the second section is made (e.g., Nitinol) and/or by the configuration of the attachment joint, which can provide mechanical biasing of the two sections relative to each other, for example. The needles can also comprise more than two separate portions, which may be made of the same or different materials.

The outer tube 12 of the ablation catheter 10 is illustrated in FIG. 2 as being partially retracted relative to the distal end of the inner tube 14 and the extending needles 20. Outer tube 12 can be made from a relatively smooth, flexible material, yet should be sufficiently strong to be able to compress the needles 20 toward the central axis of the inner tube 14 and maintain them for a period of time in this compressed condition. The inner surface of the outer tube 12 and/or the outer surface of the inner tube 14 can be relatively smooth and/or comprise a slip coating to allow the tubes to easily slide relative to each other and/or the needles 20. The outer tube 12 can optionally include one or more markers, such as marker hand 22, for example, which can provide a reference area for locating a certain point or location of the outer tube 12 relative to the other portions of the ablation catheter and/or the patient's anatomy. Such markers can additionally or alternatively be provided on the inner tube 14 and/or one or more of the needles 20. These markers may be imaging markers for use in an imaging procedure, in one embodiment.

The ablation catheters of the invention can further include a handle or other mechanism (not shown), which includes an actuating mechanism positioned proximal to the illustrated distal end of the device. Such an actuating mechanism can include one or more sliders, rollers, knobs, or the like that can be used to moved the outer tube of the device back and forth relative to the other components of the device. The ablation catheter can further include an electrical connection mechanism that provides power to the needles. This electrical connection mechanism can be provided within the inner tube for connection to the needles, for example.

As mentioned above, the ablation catheters of the invention can include more or less than the four ablation needles illustrated in this exemplary embodiment, where the number of needles is preferably selected to achieve optimum capture and closure for the leak closure process. For some applications, it may be desirable to provide a relatively small number of needles that are large or small in length and/or diameter, for example, while in other cases it may be desirable to provide a large number of needles that are large or small in length and/or diameter as part of a single ablation device. The ablation catheters can further include one or more additional lumens in either the outer tube or inner tube in order to provide steering capabilities to the distal end of the device. One or more additional lumens can also be provided for contrast injection for leak location. In yet another alternative, the central lumen 18 can be used for contrast injection, if desired. One or more additional lumens can be provided to supply one or more fluids, such as irrigation fluids or ablation fluids.

Figure 3:
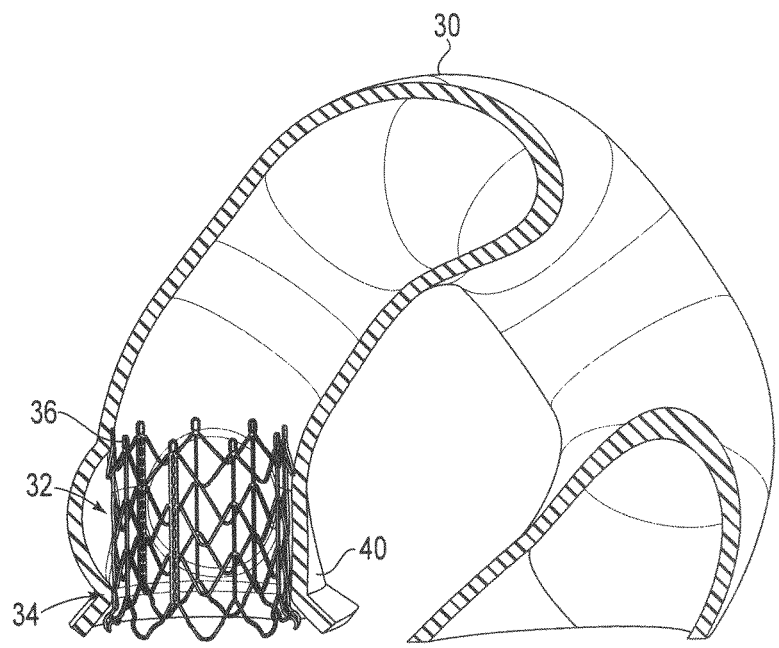
FIG. 3 is a partial cross-sectional view of a model of an aorta with a stent positioned relative to the aortic annulus.

Referring now to FIGS. 3 through 15, a method is illustrated of using an ablation catheter of the type illustrated in FIGS. 1 and 2, for example. In particular, a model of an aorta 30 is shown in FIG. 3, with a section of the aorta cut away to better view the area in which the methods of the invention are performed. The aorta 30 includes a sinus area 32 and a valve annulus 34. An exemplary stent 36 is shown in a relatively typical location, relative to the annulus 34, and more particularly, is shown in an exemplary position for an aortic valve replacement procedure. For clarity of illustration, a valve of the type that would typically be attached within the center area of the stent 36 is not illustrated: however, if the stent were being provided to replace the aortic valve, a valvular structure (either bioprosthetic or mechanical, for example) would be provided within the central open area of the stent 36.

As described above, a stent or stented valve can be delivered to the area of the aortic annulus 34 using any type of invasive or minimally invasive procedure, as desired. However, because the generally circular outer shape of the stent will typically not be identical to the inner opening of the annulus in which it is positioned (i.e., the annulus opening will typically have a somewhat irregular shape), gaps or openings may be created between the stent and the annulus after stent implantation, thereby creating a potential area for leakage. For purposes of this description, such a leak area would be present in the area indicated by reference numeral 40 (also see FIG. 5). This leak area 40 can be detected and specifically located using any of a number of visualization techniques, such as intravascular ultrasound (IVUS), transesophageal echocardiography (TEE), intracardiac echocardiography (ICE), or other available techniques. Although it is understood that there are several alternative methods and approaches that can be used to deliver this therapy with the ablation catheters of the invention, the present description is directed specifically to a transfemoral approach that utilizes a guidewire. It is understood that other approaches may alternatively be used, such as transapical, transatrial, trans-septal and transvenous approaches, for example. Further, the ablation catheter 10 can be positioned and used, for example, through a thoracotomy or sternotomy, percutaneously, transvenously, arthroscopic ally, or endoscopically. It is also contemplated that the ablation catheter can be used with open-heart surgical procedures.

Figure 4:
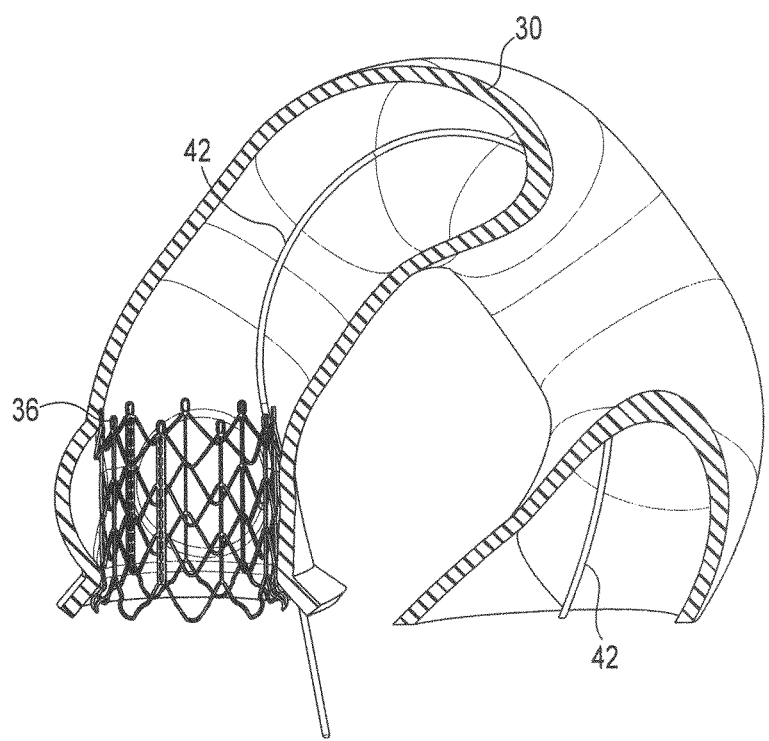
FIG. 4 is another partial cross-sectional view of the model of a stent positioned within an aorta of FIG. 3, and further illustrating a guidewire of an ablation catheter.
Figure 5:
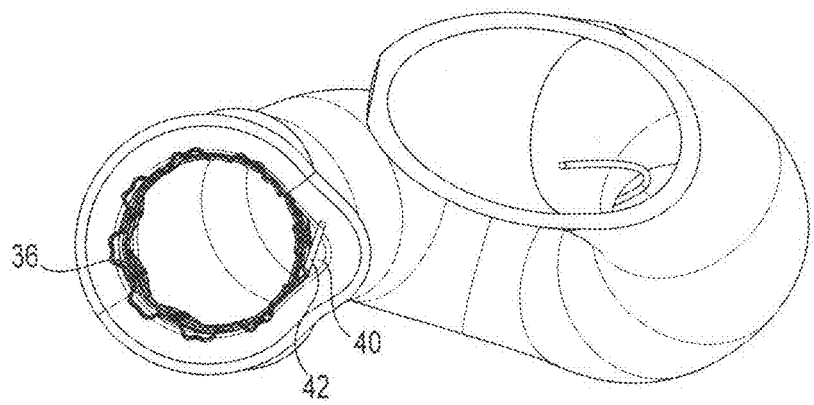
FIG. 5 is an axial view of the aorta, stent, and guidewire of FIG. 4, and which also illustrates a location of an exemplary paravalvular leak.
Figure 6:
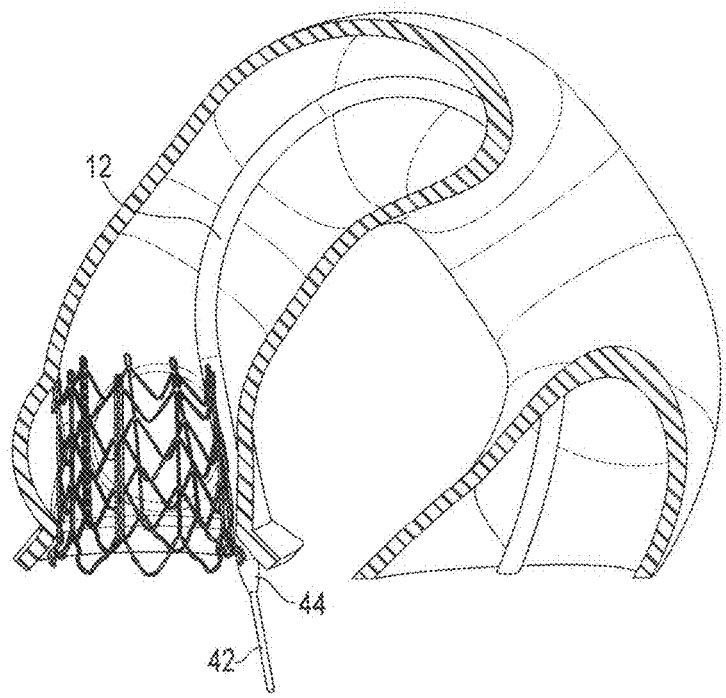
FIG. 6 is a partial cross-sectional view of the aorta model of FIG. 5, and further illustrating an outer tube and dilator of the ablation catheter in the area of the paravalvular leak.
Figure 7:
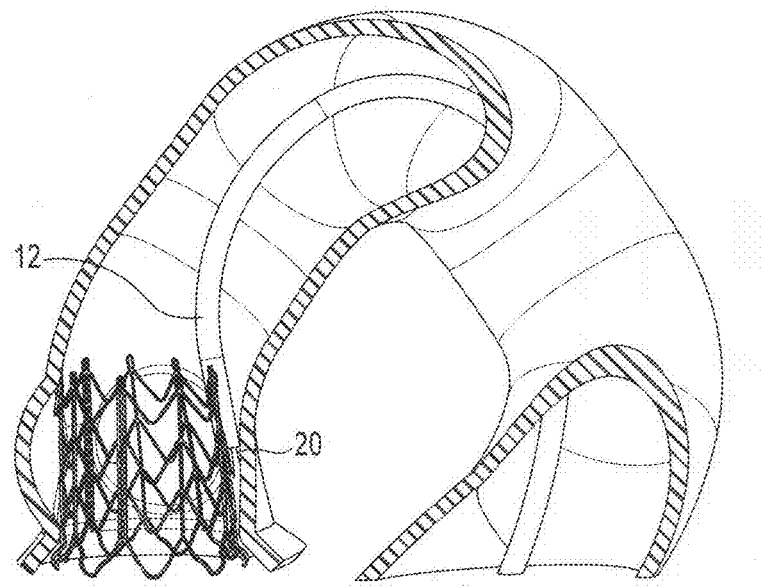
FIG. 7 is a partial cross-sectional view of the aorta model of FIG. 6, and further illustrating needle tips extending from the distal end of the outer tube of the ablation catheter.
Figure 8:
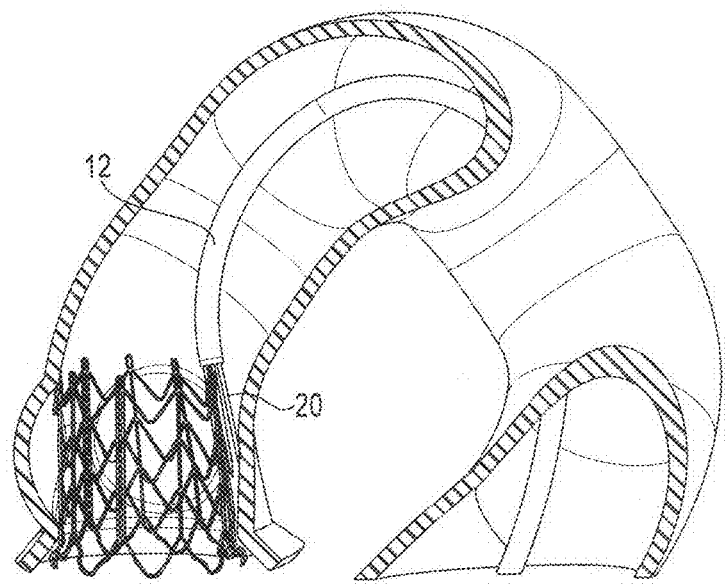
FIG. 8 is a partial cross-sectional view of the aorta model of FIG. 7, and further illustrating the outer tube in a partially retracted position relative to the needle tips.

With this exemplary transfemoral approach for repairing the paravalvular leak 40, a guidewire 42 is inserted into the femoral artery, tracked over the aortic arch, and moved to the identified leak area 40. In one exemplary method, the guidewire 42 can be guided through the leak opening 40 using a steerable catheter and one or more visual guidance techniques. FIGS. 4 and 5 illustrate an exemplary location of the guidewire 42 after its placement relative to the leak 40. In particular, FIG. 5 illustrates the guidewire 42 extending into the leak area 40, between the outer surface of the stent 36 and the inner surface of the annulus opening.

Once the guidewire 42 is in its desired position, the outer tube 12 can be moved along the guidewire 42 to the location of the leak. It is possible for this movement of the guidewire to be accomplished with the assistance of a dilator 44 (see FIG. 6), although it is also possible to guide the entire assembly in place without the use of a dilator. The dilator 44 (if any) and guidewire 42 are then removed from the patient, leaving the distal end of the outer tube 12 in the leak area 40.

The inner tube 14, with needles 20 extending from its distal end, can then be inserted into the proximal end of the outer tube 12, and guided through the length of tube 12 to its distal end. In this position, the tips of the needles 20 should be located near the distal rim of the outer tube 14 (see FIG. 7), which will be the general location of needle insertion. If the outer tube 12 is inserted past the valve and into the ventricle prior to insertion of the inner tube 14 and needles 20, it can then be backed into place relative to the valve and leak opening once the needle ends are close to the distal end of the tube 12. Alternatively, the tube 12 will not need to be hacked into place if the outer tube 12 is stopped and held in a desired deployment location during its initial placement relative to the Valve and leak opening. If the tips of the needles 20 are placed at one end of the opening of the leak, such as where it is desired to have the needle tips penetrate into the tissue (see FIG. 8), then the outer tube 12 would be backed out to a point beyond the spring-biased bend of the needles. In this way, the needles will be biased outwardly relative to the longitudinal axis of the inner tube 14. It is further desirable to place the needles in a position in which they do not interfere with any leaflets of the valved stent. In any case, the tips of at least some of the needles 20 will be adjacent to the tissue in the leak area 40.

Figure 9:
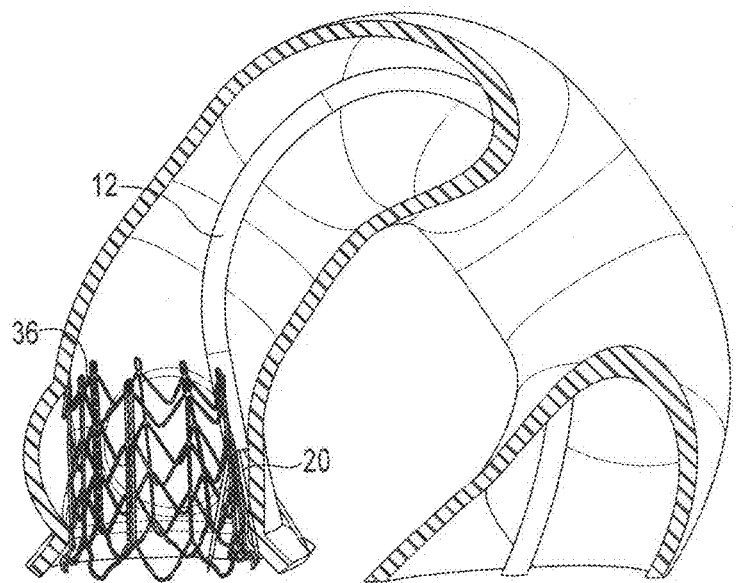
FIG. 9 is a partial cross-sectional view of the aorta model of FIG. 8, and further illustrating the positioning of the needle tips relative to the leak opening.
Figure 10:
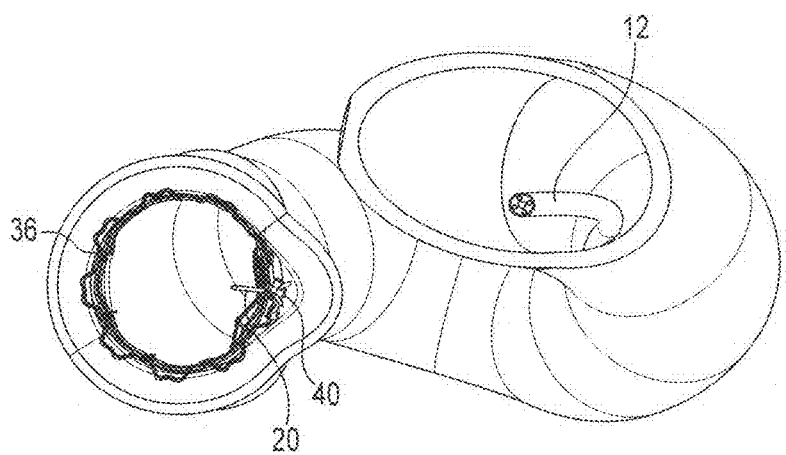
FIG. 10 is an axial view of the ablation catheter and needle tip as they are positioned in FIG. 9.

The inner tube 14 with extending needles 20 can then be pushed forward, as is illustrated in FIGS. 9 and 10, thereby allowing the needles 20 to expand outwardly relative to the longitudinal axis of the inner tube 14. Some of the needles 20 will thereby penetrate into tissue, while other needles will extend into spaces between wires of the frame of the stent 36. If it is determined, either via imaging techniques or via tactile feedback, that the ablation catheter 10 and its corresponding needles 20 are not properly positioned within the leak area and into the stent and/or surrounding tissue, the needles 20 may be repositioned one or more times in order to achieve optimal placement. In order to accomplish this repositioning, the needles 20 can be moved relative to the outer tube 12 and the opening 40 until the needles 20 are sufficiently free to be able to be moved to a new location.

In an alternative application, the needles may be inserted into just the tissue next to the stent (i.e., the needles are inserted so that they do not also extend into spaces between wires of the stent). Closure of the leakage area would then be accomplished by shrinking the tissue surrounding the stent by a sufficient amount to close or minimize the existing gap.

Figure 11:
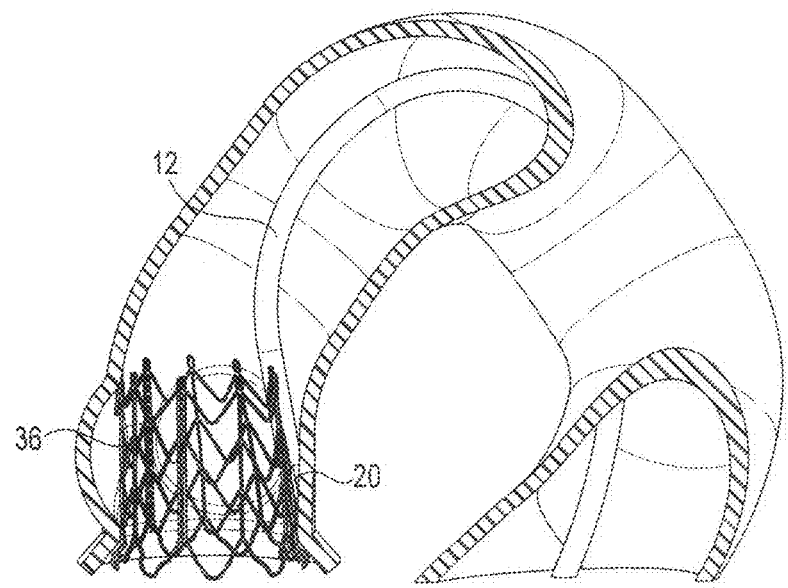
FIG. 11 is a partial cross-sectional view of the aorta model of FIG. 9, further illustrating the outer tube in a position in which it has slightly compressed the needle tips toward a central longitudinal axis of the device.
Figure 12:
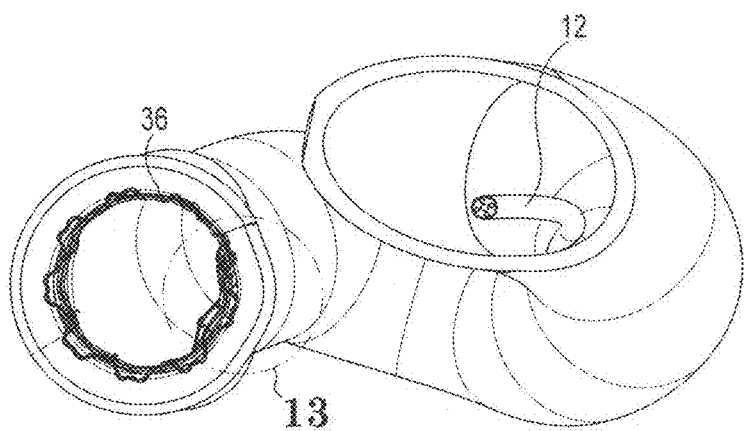
FIG. 12 is a partial axial view of the aorta, stent, and distal end of the ablation catheter of FIG. 11.

After it is determined that the needles 20 are positioned properly within the leak area, the outer tube 12 can be advanced forward to compress or move the needles 20 inwardly toward each other and the longitudinal axis of the inner tube 14, as is illustrated in FIGS. 11 and 12. Because the needles 20 will now be engaged with both the tissue and the stent, this needle movement will pull the tissue and stent closer to each other, thereby closing or minimizing the gap or leak area. Once the adjacent surfaces are determined to be close enough to each other for effective use of the device, radio frequency (RF) energy can be delivered to weld or shrink the surrounding tissue, thereby minimizing or closing the gap. The RF energy can be delivered in various alternating combinations between each needle, in one embodiment. Alternatively, the RF energy can be provided in a single application between selected needles (i.e., in a bi-polar delivery combination). Further, a ground pad can be used and/or various mono-polar delivery combinations can be employed. In general, the delivery of RF energy can be accomplished using variations of many parameters. For example, the RF energy can be applied at constant levels or the levels can moderate up and down, for short or long durations, and with or without irrigation. The delivery of energy can also be adjusted based on conditions of the tissue and/or feedback to the energy source. In one example, the power and time can be set such that the tissue temperature would be raised to approximately 85-95° C. with clamping pressure on the tissue of approximately 20 g/cm², in order to achieve adequate adhesion. However, tissue adhesion may also be possible with a lower temperature and a higher pressure. In addition, the power can be pulsed to avoid overheating of the tissue, or the power can be applied in a generally continuous manner.

The ablation catheter 10 may further include at least one temperature-sensitive element for monitoring the temperature of the device and surrounding tissue. For example, one or more thermocouple wires, thermisters, or thermochromatic inks can be used for temperature monitoring.

Figure 13:
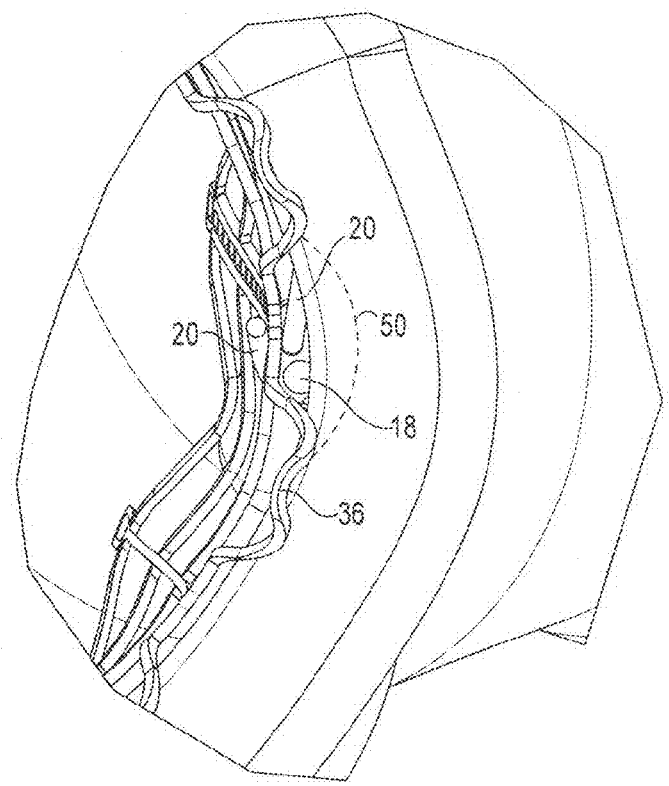
FIG. 13 is an enlarged side view of the portion of FIG. 12 indicated with a rectangle.

FIG. 13 is an enlarged side view of the portion of FIG. 12 indicated with a rectangle, which better illustrates the needles 20 as they have been pulled toward each other in the area of the leak (i.e., after the leak opening has been closed) and reference number 50 designates one illustrative positioning of the tissue relative to the stent prior to closing the leak opening. As shown in this figure, one needle 20 is positioned at least partially within the frame of the stent 36 and the other three needles 20 are at least partially penetrating the adjacent tissue. Other combinations of needle locations are possible, although it is preferable that collapsing, pulling, or pushing the needles toward each other and toward the longitudinal axis of the inner tube 14 will result in sealing or at least reducing the size of the leak. It is noted that even if the leak is not entirely sealed, the healing response created by the RF energy may be sufficient to eventually seal the leak that has been at least partially closed or minimized.

Figure 14:
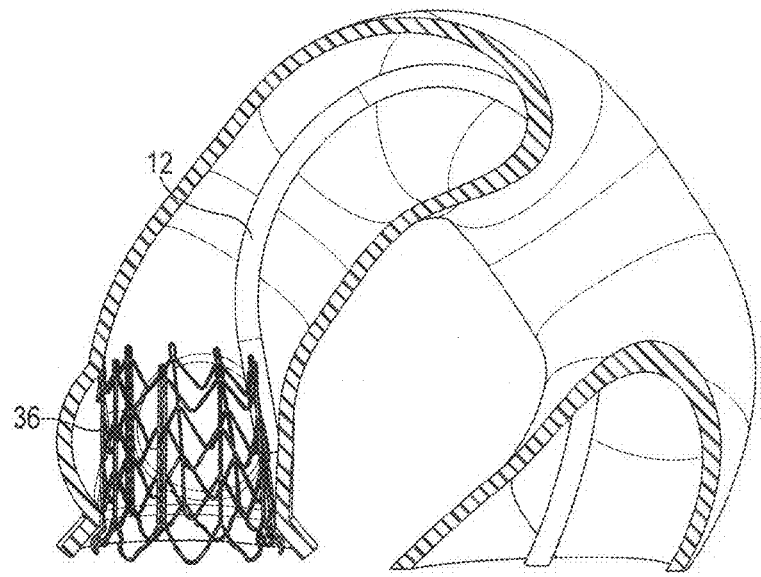
FIG. 14 is a partial cross-sectional view of the aorta model of FIG. 11, further illustrating the needles retracted into the outer tube of the ablation catheter.

After the RF welding process is complete, the needles 20 can be retracted back into the outer tube 12, as is illustrated in FIG. 14. Although penetration of the needles into the tissue may leave small holes in the tissue that are approximately the size of the needle diameter, these holes will close during the healing process. For this reason, it may be desirable to use the smallest diameter needles that will deliver the desired amount of RF energy necessary to seal the leak area.

Figure 15:
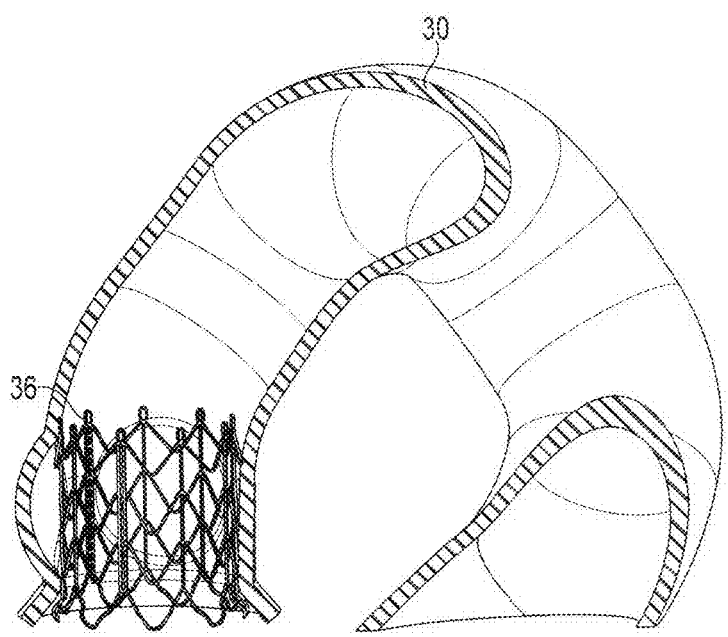
FIG. 15 is a partial cross-sectional view of the aorta model of FIG. 14 with an implanted stent positioned relative to its annulus after removal of the ablation catheter from the aorta.

After the procedure is complete, the device can be removed, as is illustrated in FIG. 15. If performed properly, the completed RF sealing process of the invention will provide a tighter seal between the stent and the wall of the structure into which it was implanted. The valve can then be tested to see if the leak has been closed or reduced. Although it is desirable that this process will eliminate all or most of the paravalvular leakage in the area surrounding the stent, even reducing the size of the leak area can provide improved performance of the implanted aortic valve.

If it is determined that the size of the leak area is still too large after performing the above-described procedure, the entire procedure can be performed again, using the same or a different ablation catheter. For example, it is contemplated that a relatively large device with many needles can be used in a first procedure to seal a first section or portion of a leak area, and then one or more smaller devices can be used adjacent to the first sealing area to further close the gap of the leak area. Devices of different sizes and configurations can be provided for single and multiple ablation procedures, where the needles can be provided with different sizes, lengths, and materials in order to close leak openings having different sizes and characteristics.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. An ablation catheter comprising:
   an inner tube comprising a length, a distal end having a distal tip, and a longitudinal axis;
   a plurality of needles extending from the distal tip of the inner tube and biased away from the longitudinal axis;
   an outer sheath slideably moveable relative to the inner tube to surround at least a portion of the length of the inner tube and its extending needles; and
   a radio frequency energy source electrically connected to the plurality of needles,
   wherein at least one of the needles comprises a distal portion, a proximal portion, and a hinge between the distal and proximal portions, and wherein the distal portion of the needle is biased outwardly relative to the proximal portion of the needle and the longitudinal axis.

2. A method of reducing the size of a space between an implanted device and an adjacent tissue within a patient, the method comprising the steps of:
   inserting an outer sheath into the patient until a distal end of the outer sheath is positioned adjacent to the space;
   inserting an inner tube into a proximal end of the outer sheath, wherein the inner tube comprises a plurality of needles extending from its distal end;
   guiding the inner tube through the outer sheath until the needles extend at least partially from the distal end of the outer sheath;
   positioning the tips of the needles adjacent to the tissue and the implanted device;
   advancing the needles until they penetrate the tissue and interface with the implanted device;
   retracting the needles at least partially relative to the sheath to pull the tissue an dim planted device closer to each other and reduce the size of the space;
   applying radio frequency energy to at east one of needles;
   retracting the needles from the tissue; and
   removing the inner tube and outer sheath from the patient.

3. The method of claim 2, further comprising the step of inserting a guide wire into the patient prior to the step of inserting the outer sheath, and then removing the guide wire after the step of inserting the inner tube.

4. The method of claim 2, wherein the step of inserting the outer sheath into the patient comprises using visualization techniques.

5. The method of claim 2, wherein the step of retracting the needles comprises advancing the outer sheath toward the distal end of the needles to compress the needles toward the longitudinal axis of the inner tube.

6. The method of claim 2, wherein the step of applying radio frequency energy comprises applying the radio frequency energy to at least one of the needles with at least two sequential applications.

7. The method of claim 2, wherein the implanted device comprises a stented valve, wherein the tissue adjacent to the stented valve comprises aortic tissue adjacent an aortic annulus, and wherein the space comprises a paravalvular leak location.

8. The method of claim 2, wherein the steps of inserting the outer sheath and inserting the inner tube into the patient comprise percutaneous insertion through an aorta of the patient.

9. A method of reducing the size of a space between an implanted device and an adjacent tissue within a patient, the method comprising the steps of:
- providing an ablation catheter comprising:
  - an inner tube comprising a distal end and a longitudinal axis;
  - a plurality of needles extending from the distal end of the inner tube and biased away from the longitudinal axis;
  - an outer sheath slideably moveable relative to the inner tube to surround at least a portion of the length of the inner tube and its extending needles; and
  - a radio frequency energy source electrically connected to the plurality of needles;
- inserting the outer sheath into the patient until a distal end of outer sheath is positioned adjacent to the space;
- inserting the inner tube with extending needles into a proximal end of the outer sheath and guiding the inner tube through the outer sheath until the needles extend at least partially from the distal end of the outer sheath;
- positioning the tips of the needles adjacent to the tissue and the implanted device;
- advancing the needles until they penetrate the tissue;
- retracting the needles at least partially, relative to the sheath to pull the tissue and implanted device closer and reduce the size of the space;
- applying radio frequency energy to at least one of needles;
- retracting the needles from the tissue; and
- removing the catheter from the patient.

* * * * *